United States Patent
Martinez et al.

[19]
[11] Patent Number: 6,126,650
[45] Date of Patent: *Oct. 3, 2000

[54] FLOW DIRECTED CATHETER HAVING RADIOPAQUE STRAIN RELIEF SEGMENT

[75] Inventors: Susana M. Martinez, Coral Gables; Boris Shkolnik, Aventura, both of Fla.

[73] Assignee: Cordis Corporation, Miami Lakes, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 09/106,966

[22] Filed: Jun. 30, 1998

[51] Int. Cl.$^7$ .................... A61M 25/098; A61M 25/00
[52] U.S. Cl. .................................. 604/529; 604/264
[58] Field of Search ................. 604/53, 93, 158, 604/164, 264–265, 280, 282, 283, 912, 529, 525; 600/433, 435

[56] References Cited

U.S. PATENT DOCUMENTS

| | | |
|---|---|---|
| 3,529,633 | 9/1970 | Vaillancourt . |
| 3,645,955 | 2/1972 | Flynn ................................. 604/280 |
| 4,282,876 | 8/1981 | Flynn ................................. 604/280 |
| 4,385,635 | 5/1983 | Ruiz . |
| 4,563,181 | 1/1986 | Wijayarathna et al. . |
| 4,581,390 | 4/1986 | Flynn ................................. 523/112 |
| 4,596,563 | 6/1986 | Pande . |
| 4,636,346 | 1/1987 | Gold et al. ......................... 604/280 |
| 4,863,442 | 9/1989 | DeMello et al. . |
| 4,898,591 | 2/1990 | Jang et al. . |
| 5,004,456 | 4/1991 | Botterbusch et al. ............. 604/280 |
| 5,017,259 | 5/1991 | Kohsai . |
| 5,078,702 | 1/1992 | Pomeranz . |
| 5,085,649 | 2/1992 | Flynn . |
| 5,178,158 | 1/1993 | de Toledo . |
| 5,221,270 | 6/1993 | Parker . |
| 5,279,596 | 1/1994 | Castaneda et al. . |
| 5,300,032 | 4/1994 | Hibbs et al. ...................... 604/164 |
| 5,300,048 | 4/1994 | Drewes, Jr. et al. . |
| 5,308,342 | 5/1994 | Sepetka et al. . |
| 5,336,205 | 8/1994 | Zenzen . |

FOREIGN PATENT DOCUMENTS

| | | |
|---|---|---|
| 0 273 618 A2 | 7/1988 | European Pat. Off. . |
| 0 303 487 A2 | 2/1989 | European Pat. Off. . |
| 196 47 280 A1 | 11/1996 | Germany . |

OTHER PUBLICATIONS

Computer Abstract of Article Entitled: "Transcatheter Injection of Silk Particulates and Line Segments in the Treatment of Cerebral Arteriovenous Malformations." Ma LT. Chung Hua Wai Ko Tsa Chih (China), Aug. 1991, pp. 516–518, 526–527.

Computer Abstract of Article Entitled: "Hepatic Arterial Embolization in Cases of Extensive Celiac Arterial Stenosis." Hori S., Inoue E., Narumi Y., Fujita M., Kadowaki K. Radiology (United States), Feb. 1991, p. 353–5.

Computer Abstract of Article Entitled: "Intracranial Thrombolysis Via a Catheter Embedded in the Clot." Jungreis CA, Wechsler LR, Horton JA. Stroke (United States), Nov. 1989, p. 1578–80.

Computer Printout of Title of Article Entitled: "Hepatic Arterial Embolization Using Flow Directed Microcatheter." Hori S, Takeuchi N., Hosoki T., Koh T., Yoshioka, Kuroda C., Mitomo M., Kozuka T., Narumi Y., Fujita M. Rinsho Hoshasen (Japan), Mar. 1988, p. 377–81.

Brochure and Instructions for Use of Cordis Corporation product, copyright 1997.

*Primary Examiner*—Sharon Kennedy
*Attorney, Agent, or Firm*—Henry W. Collins

[57] ABSTRACT

A flow directed catheter for use in medical diagnostic or therapeutic procedures having a strain relief segment between the relatively stiff proximal section of the catheter and the floppy distal tip portion in which the strain relief segment is formed of a polymeric material containing a radiopaque agent.

8 Claims, 2 Drawing Sheets

U.S. PATENT DOCUMENTS

| | | |
|---|---|---|
| 5,496,291 | 3/1996 | Spencer . |
| 5,496,294 | 3/1996 | Hergenrother et al. . |
| 5,531,715 | 7/1996 | Engelson et al. . |
| 5,533,985 | 7/1996 | Wang . |
| 5,538,510 | 7/1996 | Fontirroche et al. . |
| 5,538,512 | 7/1996 | Zenzon et al. . |
| 5,545,151 | 8/1996 | O'Connor et al. . |
| 5,584,821 | 12/1996 | Hobbs et al. . |
| 5,588,964 | 12/1996 | Imran et al. . |
| 5,599,325 | 2/1997 | Ju et al. . |
| 5,599,326 | 2/1997 | Carter . |
| 5,601,538 | 2/1997 | Deem . |
| 5,658,264 | 8/1997 | Samson . |
| 5,704,926 | 1/1998 | Sutton . |
| 5,766,202 | 6/1998 | Jones et al. ............................ 606/196 |
| 5,838,879 | 11/1998 | Tanabe et al. ......................... 604/280 |
| 5,895,378 | 4/1999 | Berenstein et al. .................... 604/280 |
| 5,921,978 | 7/1999 | Thompson et al. ..................... 604/529 |

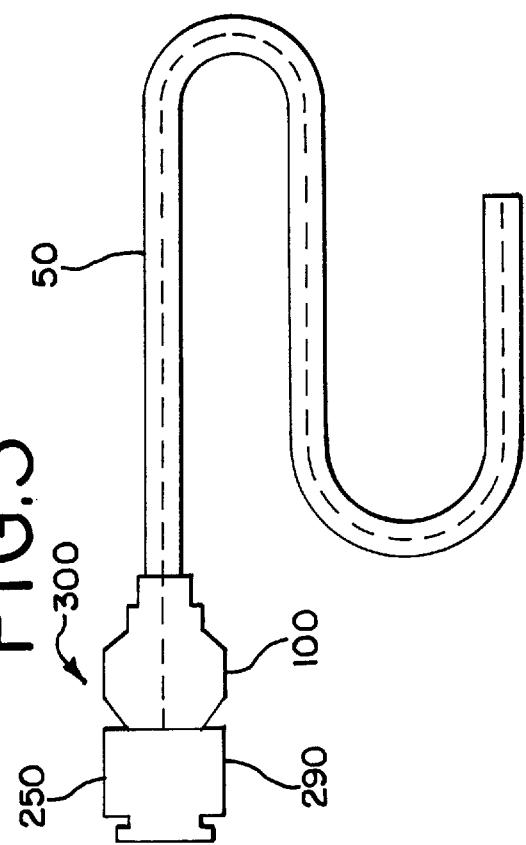
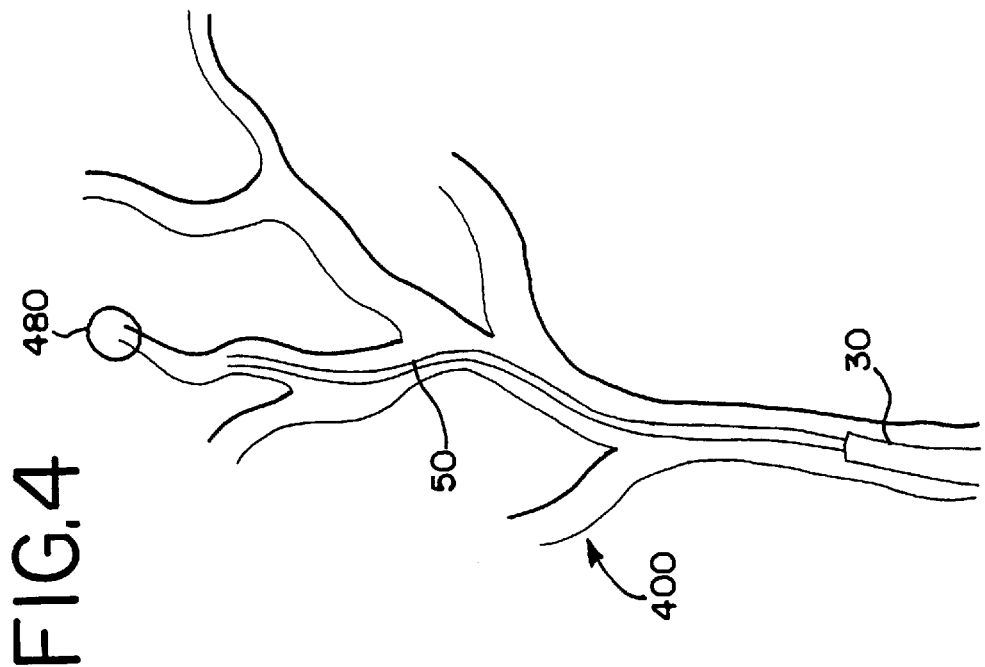

FLOW DIRECTED CATHETER HAVING RADIOPAQUE STRAIN RELIEF SEGMENT

BACKGROUND OF THE INVENTION

1. Field of the Invention

A flow directed catheter for use in medical diagnostic or therapeutic procedures having a strain relief segment between the relatively stiff proximal section of the catheter and the floppy distal tip portion in which the strain relief segment is formed of a polymeric material containing a radiopaque agent.

2. Background Art

In order to diagnose the extent of coronary artery disease angiography procedures are used to view the blood flow through selected blood vessels. In carrying out this procedure diagnostic catheters are introduced into the blood vessels of a patient and are advanced over a guidewire through the vascular system of the patient until the distal end of the catheter is steered into the particular blood vessel to be examined.

In view of the fact that the human vasculature is quite tortuous it is essential that a diagnostic catheter be capable of being steered by torquing the proximal hub of the catheter in order to direct the catheter through the vascular system. With extremely small vessels it is often not possible to provide a catheter with sufficient flexibility for passage through the tortuous vasculature while still providing sufficient rigidity to steer, or torque, the distal end of the catheter to a desired site. Accordingly, in certain instances it is desirable to provide a catheter in which the proximal end of the catheter is relatively stiff and the distal end of the catheter is very flexible, or floppy, in order that the distal tip of the catheter may be steered, or directed, through the vasculature by means of the flow of blood through the vessel. Such catheters are generally referred to as flow directed catheters.

Such flow directed catheters generally comprise a connector hub, a relatively long and stiff proximal section for pushing the catheter into the vasculature system, and a shorter and very floppy distal tip section. The floppy distal tip section is of a very low durometer in order that the tip section may be guided, or directed, by the flow of blood through the blood vessel.

Medical catheters have for many years included a relatively short distal tip which is formed of a polymeric material containing a radiopaque agent in order that the distal tip of the catheter may be readily viewed under X-ray radiation as the catheter is passed through the blood vessels of a human body. With a radiopaque distal tip it is possible for the physician to observe the exact location of the distal tip portion of the catheter relative to its position within the human body.

Examples of prior art patents which disclose medical catheters having distal tips containing a radiopaque agent are U.S. Pat. No. 5,045,072 entitled "Catheter Having Highly Radiopaque, Flexible Tip" to Castillo et al. and U.S. Pat. No. 5,171,232 to entitled "Catheter Having Highly Radiopaque, Flexible Tip" Castillo et al., both of which are assigned to the assignee of the present application and are incorporated herein by reference.

One problem with currently available flow directed catheters is that with these devices the physician is unable to determine the exact position of the transition area between the relatively stiff proximal portion of the catheter and the floppy distal portion of the catheter. With the inability to determine the location of this transition area it is very difficult to determine which portion of the catheter may be steered by torquing on the hub of the catheter and which portion of the catheter may not be so steered but may simply be permitted to be directed by the flow of blood through the blood vessel. In addition, it is difficult for the doctor to prevent kinking of the relatively soft floppy portion of the catheter as this portion of the catheter passes through the blood vessel if the doctor is unable to discern whether a particular portion of the catheter is formed of a relatively stiff material or a very floppy material.

SUMMARY OF THE INVENTION

The present invention relates to a flow directed catheter intended for the insertion into the blood vessels of a patient which may be guided through the vasculature of the patient by a force exerted on the floppy distal portion of the catheter by the flow of blood through the vasculature. The catheter includes a strain relief section which is positioned between a relatively rigid proximal portion of the catheter and a floppy distal portion of the catheter and in which the strain relief section is formed of a polymeric material containing a radiopaque agent with this device, the physician may readily determine the exact position of the strain relief portion of the catheter or the position of the transition region between the relatively stiff portion of the catheter and the very floppy distal portion of the catheter.

Flow directed catheters constructed in accordance with the present invention include a proximal connector hub, a relatively stiff proximal tubular section bonded to the hub, a highly flexible distal tubular section, and a relatively short tubular strain relief section interposed between the proximal tubular section and the distal top section. The tubular strain relief section is more flexible than the proximate tubular section and less flexible than the distal tubular section and is formed of a polymeric material containing a radiopaque agent. With this device, a physician is able to precisely locate the position of the strain relief section of the catheter. The highly flexible tubular section is very floppy in nature and its position is controlled by the flow of blood through the blood vessel to thereby permit the physician to precisely position the distal tip of the catheter at a desired site.

In accordance with another aspect of the present invention, the tubular strain relief section is formed of a polymeric material containing from about 40 to 75 weight percent of radiopaque agent, such as barium sulfate, bismuth subcarbonate or bismuth trioxide.

In accordance with still another aspect of the present invention, the tubular strain relief section is thermally fused to the distal end of the proximal tubular section and the distal tubular section is thermally fused to the distal end of the strain relief section. In addition, the tubular strain relief section is preferably free of any metallic radiopaque member, such as a metal ring, which is positioned on or adjacent to the strain relief section.

In accordance with another aspect of the present invention, the highly flexible distal section, or floppy distal tip, is more than twenty times the length of the strain of the relief section and the relatively stiff proximal section of the catheter is more than ten times the length of the floppy distal section. In addition, the proximal tubular section preferably has a durometer of between 60 D and 90 D, the strain relief section has a durometer of between 25 D and 50 D and the distal tubular section has a durometer between 50 A and 90 A.

In accordance with still another aspect of the present invention, the distal floppy section has a length of between 10 and 50 centimeters and may be comprised of an inner distal section and an outer distal section in which the inner distal section is more flexible than the strain relief section of the catheter and the outer distal section is more flexible than the inner distal section.

From the above it may be appreciated that one object of the invention is a flow directed catheter with a floppy distal tip which may be directed through the vasculature by the flow of blood and in which a radiopaque strain relief section is positioned between the floppy distal tip and a relatively stiff proximal section to thereby provide the physician with an exact location of the transition area between the relatively stiff proximal section and the floppy distal tip of the catheter. This and other objects, advantages and features of the invention will become better understood from a detailed description of the invention which is described in conjunction with the accompanying drawings:

BRIEF DESCRIPTION OF THE DRAWINGS

FIG. 3 is an elevational view of the flow directed catheter of FIG. 1 in conjunction with the flushable stylet of FIG. 2; and, FIG. 4 is diagrammatic view showing the flow directed catheter of the present invention inserted in the tortuous vasculature of a human body.

DETAILED DESCRIPTION OF A PREFERRED EMBODIMENT

Figure 1:
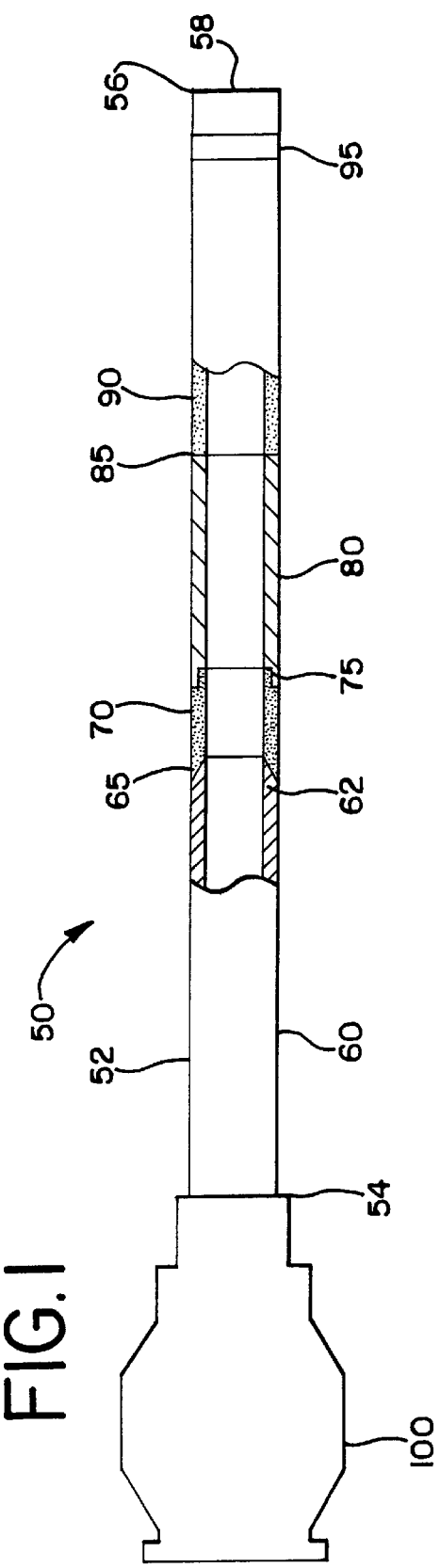
FIG. 1 is a partially crossed-sectional view of the flow directed catheter of the present invention which illustrates the various section of the catheter.

FIG. 1 illustrates the assembled flow directed catheter 50 having a main tubular body 52 with a proximal end 54 and a distal end 56 and an inner lumen 58 extending there through. The main tubular body 52 is constructed from four segments; a relatively stiff proximal shaft segment 60, a radiopaque strain relief segment 70, a proximal floppy segment 80 and a soft distal floppy segment 90.

The relatively stiff proximal shaft segment 60 of main tubular body 52 is preferably made from a high durometer polymeric material or a polymer coated metallic hypotube. Suitable polymers for the proximal shaft segment 60 include biologically compatible polymers such as nylon, polyethylene, polyester, polyurethane, silicone and the like. The durometer of the proximal shaft segment 60 is between 60 D and 90 D and is preferably 75 D. The proximal shaft segment 60 provides proximal support for flow directed catheter 50, enabling pushability without the need of a guidewire. The proximal shaft segment 60 comprises a proximal end 54 to which a hub coupling 100 is attached and a slight distal taper 62 to which the radiopaque strain relief segment 70 is attached. The length of proximal shaft segment 60 is between 100 cm and 145 cm preferably between 125 cm and 130 cm. The preferable inner diameter and outer diameter of proximal shaft segment 60 are about 0.55 mm and 0.94 mm respectively. The length of the slight distal taper 62 is between 0.1 mm and 3 mm more preferably between 1.5 mm and 2.5 mm.

The proximal shaft segment 60 is attached to the radiopaque strain relief segment 70 at the slight distal taper 62 by a thermal fuse joint 65. The thermal fuse joint 65 is created by placing the slight distal taper 62 of proximal shaft segment 60, while on a mandrel, inside of the radiopaque strain relief segment 70 and heating the assembly. Depending upon the materials used for the proximal shaft segment 60 and the radiopaque train relief segment 70 the fusing temperature ranges from 300° F. to 550° F. Preferably the fuse temperature is between 350° F. and 450° F.

The radiopaque strain relief segment 70 provides the physician with a visible marker under fluoroscopy indicating the location of the relatively stiff proximal shaft segment 60 in relation to the guiding catheter tip. The radiopaque strain relief segment 70 also prevents kinking that occurs when a rigid tube is connected to a very flexible tube. The radiopaque strain relief segment 70 is more flexible than the proximal shaft segment 60 and made from a polymer tube that has been made radiopaque by incorporating radiopaque fillers during the forming process. The strain relief segment 60 is of a durometer of between about 25 D and 50 D and is preferably about 40 D. Suitable fillers include powders made from metals such as tungsten and tantalum as well as compounds containing barium and bismuth such as barium sulfate, bismuth subcarbonate and bismuth trioxide. Preferably the strain relief segment 60 is formed of a polymeric material containing between 40 and 75 weight percent of the radiopaque agent. Since the incorporation of fillers generally increase the stiffness of a polymer the length of the radiopaque strain relief segment 70 must be fairly small, between 0.4 cm and 0.6 cm preferably about 0.5 cm.

The radiopaque strain relief segment 70 is attached to a proximal floppy segment 80 by a thermal fuse joint 75. The proximal floppy segment 80 is more flexible, i.e. lower durometer than the radiopaque strain relief segment 70 and proximal shaft segment 60. The inner diameter of the radiopaque strain relief segment 70 and the proximal floppy segment 80 is between 0.25 mm and 0.55 mm preferably about 0.42 mm, while the outer diameter is between 0.60 mm and 0.94 mm preferably about 0.79 mm. The length of the proximal floppy segment 80 is between 10 cm and 20 cm preferably about 15 cm.

The proximal floppy segment 80 is attached to the distal floppy segment 90 by a thermal fuse joint 85. The distal floppy segment 90 is constructed from a low durometer polymer and is more flexible than the proximal floppy segmentile the outer diameter is between 0.25 mm and 0.76 mm preferably 0.61 mm. The length of the distal floppy segment is between 10 cm and 30 cm preferably about 20 cm. To make the distal tip of flow directed catheter 50 visible under fluoroscopy a radiopaque marker 95 is attached to distal floppy segment 90. To facilitate access to some vessels in tortuous anatomy the distal tip of the distal floppy segment 90 may be preshaped. The proximal floppy segment 80 is of a duromter between about 50 A and 90 A and preferably between about 70 A and 80 A. The distal floppy segment 90 is of a durometer of between about 50 A and 90 A and is preferably between about 65 A and 75 A.

To reduce damage while using, the flow directed catheter 50 is coated with a lubricious polymer. This coating may be hydrophobic or hydrophilic in nature, preferably hydrophilic, and applied to the interior and exterior of flow directed catheter 50. Hydrophilic coatings are widely known in the industry and may be applied using a dip coating process and subsequently dried, covalently bonded and crosslinked using a single thermal drying cycle. Preferably this drying temperature would be below the softening point of the polymers being coated about 50° C. to 60° C. To facilitate the introduction of flow directed catheter 50 into the guiding catheter a stylet is inserted to provide support.

Figure 2:
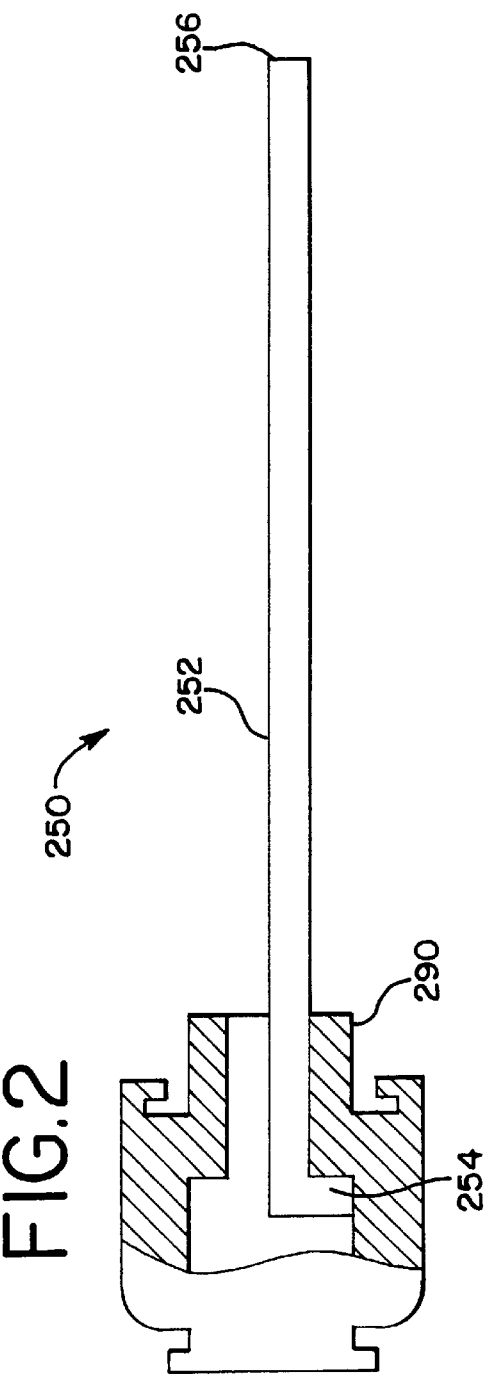
FIG. 2 is a partially crossed-sectional view of a flushable stilt for use with the flow directed catheter of FIG. 1.

FIG. 2 illustrates a flushable stylet 250 for use with flow directed catheter 50. The flushable stylet 250 allows the hydrophilic coating on the interior of flow directed catheter 50 to be flushed and hydrated without removing the stylet. This procedure prevents damage to the interior coating of the flow directed catheter 50. Flushable stylet 250 consists of a hollow tube body 252, with a proximal end 254 to which a luer hub 290 is attached and having a distal end 256. The proximal end 254 of the tube body 252 is attached to luer hub 290 by using an adhesive or thermal fuse with the lumen of luer hub 290 remaining open. The tube body 252 may be coated with a hydrophobic or hydrophilic lubricious polymer, preferably hydrophobic. To facilitate introduction of the flushable stylet 250 into flow directed catheter 50, the tube body 252 may also be tapered.

FIG. 3 illustrates the catheter sytlet assembly 300. The flushable stylet 250 is placed inside of flow directed catheter 50 coaxially. Luer hub 290, secures onto hub coupling 100. A syringe filled with saline attaches to luer hub 290 and saline is infused through luer hub 290 and into flow directed catheter 50.

FIG. 4 illustrates the flow directed catheter 50 inserted into the vasculature 400. Guiding catheter 30 is located in the vascular territory 400 proximal to the intended embolization site 480. In general the intended embolization site 480 is a region of relatively high flow as associated with an arteriovenous malformation or fistula. Flow directed catheter 50 is extended from the guiding catheter 30 and traverses the vasculature 400 towards the intended embolization site 480. Once the intended embolization site 480 is reached various types of therapeutic agents such as platinum coils, polyvinylalcohol particles, ethanol or cyanoacrylate adhesives may be delivered to treat the lesion. For regions of low flow, flow directed catheter 50 may be used in conjunction with a guidewire inserted in the lumen to access lesions.

Those skilled in the art will appreciate that the flow directed catheter of the present invention may be manufactured from various materials and with various durometers to suit the desires of different physicians.

Various modification and changes in detail may be made to the above-described embodiments and examples without departing from the spirit and scope of the invention. It is therefore intended that all such matter as described in the foregoing description and shown in the attached drawings be considered as illustrative only and not limiting.

That which is claimed is:

1. A flow directed catheter comprising a proximal connector hub, a relatively stiff proximal tubular section bonded to the hub, a highly flexible distal tubular section and a relatively short tubular strain relief section interposed between the proximal tubular section and the distal tip section, said tubular strain relief section being more flexible than the proximal tubular section and less flexible than said highly flexible distal tubular section and being formed of a polymeric material containing from 40% to 75% by weight radiopaque agent such that said tubular strain relief section is more visible to X-rays than either said proximal tubular section or said highly flexible distal tubular section thereby to provide a physician or other medical person with an exact location of said tubular strain relief section between said relatively stiff proximal section and said highly flexible distal tubular section when the inserted catheter is viewed under X-ray radiation.

2. The flow directed catheter as defined in claim 1, wherein the tubular strain relief section is thermally fused to the distal end of the proximal tubular section and the distal tubular section is thermally fused to the distal end of the tubular strain relief section.

3. The flow directed catheter as defined in claim 1, wherein the highly flexible distal section is more than twenty times the length of the strain relief section and the relatively stiff proximal section is more than 10 times the length of the highly flexible distal section.

4. The flow directed catheter as defined in claim 1, wherein the proximal tubular section has a durometer of between 60 D and 90 D, the strain relief section has a durometer of between 25 D and 50 D and the distal tubular section has a durometer of between 50 A and 90 A.

5. The flow directed catheter as defined in claim 4, wherein the distal tubular section has a length of between 10 and 50 centimeters.

6. The flow directed catheter as defined in claim 5, wherein the distal tubular section is comprised of a proximal segment and a distal segment and the proximal segment is more flexible than the strain relief section and the distal segment is more flexible than the proximal segment.

7. The flow directed catheter as defined in claim 1, wherein said tubular strain relief section has a length between 0.4 cm. and 0.6 cm.

8. The flow directed catheter as defined in claim 1, wherein said catheter has a distal tip and said distal tip has a radiopaque marker.

* * * * *